(12) United States Patent
Ruehe et al.

(10) Patent No.: US 8,435,625 B2
(45) Date of Patent: May 7, 2013

(54) PATTERNED SHEET PRODUCTS

(75) Inventors: Andreas Ruehe, Schulhausstrasse (CH); Kristel Van Impe, Zug (CH); Matthias Hauser, St. Augustin (DE); Pietro Rosato, Leverkusen (DE)

(73) Assignee: Johnson & Johnson GmbH (DE)

( * ) Notice: Subject to any disclaimer, the term of this patent is extended or adjusted under 35 U.S.C. 154(b) by 1285 days.

(21) Appl. No.: 10/555,167

(22) PCT Filed: Apr. 30, 2004

(86) PCT No.: PCT/EP2004/004627
§ 371 (c)(1),
(2), (4) Date: May 30, 2008

(87) PCT Pub. No.: WO2004/097096
PCT Pub. Date: Nov. 11, 2004

(65) Prior Publication Data
US 2008/0318004 A1    Dec. 25, 2008

(30) Foreign Application Priority Data

May 1, 2003 (EP) .................................. 03076322
May 5, 2003 (EP) .................................. 03076372

(51) Int. Cl.
*B32B 3/00* (2006.01)
*B32B 5/14* (2006.01)

(52) U.S. Cl.
USPC ............ 428/156; 428/170; 428/171; 428/172

(58) Field of Classification Search .................. 428/156, 428/170, 171, 141, 167, 172, 187; 442/327, 442/408, 400
See application file for complete search history.

(56) References Cited

U.S. PATENT DOCUMENTS

| | | | |
|---|---|---|---|
| 4,127,637 A | 11/1978 | Pietrniak et al. | |
| 4,529,480 A | 7/1985 | Trokhan | |
| 4,718,152 A | 1/1988 | Imai et al. | |
| 5,618,610 A * | 4/1997 | Tomita et al. ................ | 428/152 |
| 6,420,013 B1 | 7/2002 | Ho-Kleinwaechter et al. | |
| 2003/0019088 A1 | 1/2003 | Carter | |

FOREIGN PATENT DOCUMENTS

| | | |
|---|---|---|
| EP | 032366 B1 | 11/1998 |
| EP | 0705932 B1 | 2/2002 |
| EP | A1209270 A1 | 5/2002 |
| JP | 2003/70707 A | 3/2003 |
| JP | 2003070707 A * | 3/2003 |
| WO | WO 97/19808 A1 | 6/1997 |
| WO | WO 0171081 A1 | 9/2001 |

OTHER PUBLICATIONS

International Search Report, 2004.

\* cited by examiner

*Primary Examiner* — Catherine A Simone

(57) ABSTRACT

This invention concerns patterned sheets for cleansing and other applications, of porous or absorbent material, in particular of a non-woven material, such as a wipe. It further relates to such a sheet to which a composition has been applied. The invention further concerns the manufacture and use of such products.

15 Claims, No Drawings

PATTERNED SHEET PRODUCTS

This application is the national stage filing under USC 371 of international application PCT/EP2004/04627 filed Apr. 30, 2004.

FIELD OF THE INVENTION

This invention concerns patterned sheets for cleansing and other applications, of porous or absorbent material, in particular of a non-woven material, such as a wipe. It further relates to such a sheet to which a composition has been applied. The invention further concerns the manufacture and use of such products.

BACKGROUND OF THE INVENTION

Wipe products have become an important product category that has found a wide variety of applications for adults and babies. Examples include face or body cleansing wipes, wipes for skin treatment, and skin conditioning wipes. Over the last couple of decades so-called wet wipes have become successful as products particularly suited for these applications. These products typically are manufactured by impregnating sheets made of non-woven fabric with a suitable lotion.

Recent innovations in the wipes area included improvements in the fabric, in the impregnating liquid as well as in product presentation.

Initially, wet wipe products were made of traditional non-woven materials based on paper making technology (pulp based products). These products were well accepted but deficient in softness of the fabric material. The introduction of the 'spunlace' non-woven technology offered products that, compared to traditional paper based products, were superior in terms of softness, and also strength. This is mainly due to (i) the use of long soft fibres (most frequently rayon and PET/PP or a mixture of these fibres) in the spunlace process and (ii) the fact that during the spunlace process no binder is added to the fabric.

Apart from these developments, wipe products have been embossed or apertured mainly for aesthetic reasons. EP-A-705932 discloses non-woven fabrics having a planar background portion and at least one raised portion forming a three-dimensional pattern projected out of the plane of the background portion, wherein the base weight of the raised portion or portions is equal greater than the weight of the background portion. EP-A-1032366 discloses personal cleansing wipes comprising a substrate from hydro-entangled fibers having a three-dimensional pattern wherein the density of the raised fibrous regions is the same as the density of the base surface, and an aqueous cleansing composition.

In addition to the above lotions have been developed which offered skincare benefits in addition to the basic cleansing properties of the wipe. One approach was the introduction of lotions that were based on oil-in-water emulsions which delivered useful properties such as superior mildness, moisturization, protection and skin smoothness, when compared to simple aqueous cleansing formulations. Another approach encompassed the incorporation of active skincare ingredients, e.g. chamomile, into simple aqueous formulations, thereby delivering useful properties such as soothing. Current wet wipe products still are based on these approaches in that they are impregnated with either aqueous lotions or with oil in water emulsions.

This is in particularly required in wipes for personal cleansing and in particular in wipes used for babies and infants. In the latter instance wet wipes are used for cleansing the perineal region when changing diapers. Inadequate cleaning not only results in personal discomfort but also gives rise to diaper rash and other infection related phenomena. It has been shown that the most effective way of preventing diaper rash is to cleanse the skin thoroughly and to remove the microorganisms that have been identified as causative. The source of these microorganisms is often the fecal deposits that can remain on a baby's skin while wearing the diaper. Because fecal deposits consist of both water-soluble and oil-soluble matter, however, complete removal of fecal deposits from the diaper area requires both water-based and oil-based cleansing agents.

Another object of this invention is to provide products for cleansing and other applications that allow convenient and quick application, are easy to carry, as well as an easier and more evenly distribution of the ingredients in or on the product. They moreover should be convenient for application on babies and children.

Irrespective of its end use the softness of the wipe product is of primary importance to the consumer. Softness of the wipe material on the one hand and perceived softness of the skin after usage of the wipe on the other hand are important consumer benefits. This in particular is the case for applications on babies.

A second approach in improving the softness of non-woven fabrics is to add fabric softeners to either the finished product or to the fibres used as raw materials. This approach has been taken in many applications of dry non-wovens. Particularly in dry facial tissue products and toilet paper the softness has been significantly improved via the addition of 'fabric softeners'. Most of these softeners are silicon-based compounds or derivatives thereof.

In spite of these improvements there is still a need to improve softness of wipe products. Providing such products is an object of this invention.

These objects are attained by the sheet products of this invention that show increased softness.

SUMMARY OF THE INVENTION

The present invention is concerned with a porous or absorbent sheet comprising a substrate wherein a substantial portion of one or both surfaces of the sheet has a three-dimensional pattern embossed therein, said pattern comprising a series of raised and lowered regions, wherein the basis weight of the raised regions is essentially the same as the basis weight of the lowered regions and wherein the density of the raised regions is lower than the density of the lowered regions.

Further, the present invention is concerned with a porous or absorbent sheet comprising a substrate wherein a substantial portion of one or both surfaces of the sheet has a three-dimensional pattern embossed therein, said pattern comprising a series of raised and lowered regions, wherein at least one of the raised and/or lowered regions has no flat portion or has less flat portions than non-flat portions and/or wherein the total area covered by the flat portion(s) of a raised or lowered region is smaller than the area covered by the non-flat portion(s) of said raised or lowered region, and wherein the basis weight of the raised regions is essentially the same as the basis weight of the lowered regions and wherein the density of the raised regions is lower than the density of the lowered regions.

Also, the present invention refers to a porous or absorbent sheet comprising a substrate wherein a substantial portion of one or both surfaces of the sheet has a three-dimensional pattern embossed therein, said pattern comprising a series of raised and lowered regions, wherein none of the raised or lowered regions has any flat portion, and wherein the basis weight of the substrate is the same over the whole surface and wherein the density of the raised portions/regions is lower than the density if the lowered portions/regions.

Moreover, the present invention relates to a porous or absorbent sheet obtained by:
  providing a precursor substrate,
  providing a forming member, having an image surface, and having a three-dimensional pattern engraved therein, said pattern comprising a series of raised and lowered regions,
  advancing said precursor substrate onto said three-dimensional transfer device, and applying hydraulic energy to said precursor substrate to simultaneously entangle the fibers of the precursor substrate to finish the substrate and impart a three-dimensional pattern to the substrate comprising a series of raised and lowered regions, wherein the basis weight of the raised regions is essentially the same as the basis weight of the lowered regions and wherein the density of the raised regions is lower than the density of the lowered regions.

The forming member, in particular its image surface, preferably is moving in the direction of the movement of the precursor substrate while the three-dimensional pattern is imparted to said substrate. In case the forming member represents a forming cylinder this cylinder preferably rotates in the direction the precursor substrate is moving.

In a preferred embodiment the basis weight of the substrate is the same over the whole surface.

The substrate of the porous or absorbent sheet in general comprises a non-woven material. For the basis weight to be essentially the same over the raised and lowered regions or over the whole surface of the sheet, respectively, a tolerance range from about ±10 g/m², in particular from about ±5 g/m², is applicable due to the metering precision.

In the meaning of the present invention a raised or lowered region has less flat portions than non-flat portions if the total surface of a raised/lowered region being non-flat is larger than the total area of the raised/lowered region which is flat.

It is particularly preferred that the cross-sections of at least a portion of at least one lowered region predominantly exhibit a rounded shape being at least partially flattened at its bottom part. Sheets being equipped with the aforementioned lowered regions are very reliably to manufacture and still contribute to the general inventive design. In particular, the majority, more preferably essentially all lowered regions exhibit a rounded shape being flattened at its bottom part.

A flattened surface in the meaning of the present invention refers to a surface, in particular of the lowered region, which still has rounded portions and which is not essentially flat over its entire surface.

In another aspect of the present invention a sheet is provided wherein the three-dimensional pattern is present over the whole surface of the sheet and wherein the embossed pattern may be present at one surface or at both surfaces of the sheet.

Preferably, the three dimensional pattern is present over the whole surface of the sheet. The embossed pattern may be present at one surface or at both surfaces of the sheet.

In certain embodiments of this invention, the raised and lowered regions are located adjacent to one another. A lowered region is followed by a raised region, followed by a lowered region, and so forth. In particular, the raised and lowered regions form one or more patterns that are present at one or at both surfaces of said sheet, wherein different patterns are adjacent to one another or are separated by areas that have no pattern.

In certain embodiments of this invention, the shape of the raised and lowered regions is about identical, or identical. In specific embodiments the shape and size of the raised and lowered regions is about identical, or identical. In more specific embodiments of this invention the lowered and raised regions are arranged in a recurrent pattern of lowered and raised regions of about the same size and shape.

In still further specific embodiments, the raised and lowered regions form a pattern of lines or stripes. In particular, these lines run in one direction continuously from one side of the sheet to the other side.

In a particular aspect, at least a section of one or both surfaces of the sheet has a ridged pattern. Accordingly, the present invention is concerned with a porous or absorbent sheet comprising a substrate wherein a substantial portion of one or both surfaces of the sheet is ridged. The ridged surface is comprised of a three dimensional pattern embossed in the substrate of the sheet, said pattern comprising a repetitive series of raised and lowered regions, wherein the raised and lowered regions have the shape of lines or stripes, having equal or about equal width, and having equal or about equal size, wherein none of the raised or lowered regions has any flat portion, and wherein the basis weight of the substrate is the same over the whole surface and wherein the density of the raised portions is lower than the density of the lowered portions.

Preferably, the pattern of the lowered and raised regions runs in the machine direction by which the sheet is produced. Alternatively, the pattern of raised and lowered regions runs in the cross direction. In specific embodiments, the raised and lowered regions run in parallel.

According to another embodiment it is particularly preferred that the raised and lowered regions form a pattern of lines or stripes and that, preferably, these stripes or lines run in one direction continuously from one side of the sheet to the other side and, preferably, run in the machine direction or, in particular, in the cross direction by which the sheet is produced. The term machine direction in general refers to the manufacturing direction with which the substrate, in particular the non-woven substrate, is made, and from which the sheets according to the present invention are obtained, e.g. by cutting.

In general, if the pattern of raised and lowered regions runs in the machine direction the lines or stripes forming the raised and lowered regions run in the cross direction.

Thus in a specific aspect, this invention is concerned with a sheet as specified herein, having a recurrent pattern of raised and lowered regions, said regions taking the form of lines or stripes continuously running in parallel from one side of the wipe to the other.

Examples of such patterns are those comprising a series of lowered and raised regions that follow a wave pattern, a zigzag pattern, or a pattern of multiple lines or stripes.

Of particular interest are embodiments wherein at least one of the surfaces of the sheet in a transversal section has a sinusoidal shape.

In a further aspect, the invention provides a sheet as defined herein wherein the width of the lowered and of the raised regions is substantially the same over the whole surface of the sheet. Of particular interest are sheets wherein the width of the raised regions is about equal to that of the width of the lowered regions.

According to another aspect of the invention the porous or absorbent substrate is a non-woven material, preferably a non-woven material obtained by carding, spunlaying, the meltblowing, airlaying, wetlaying or a mixture thereof as the web forming process and by hydro-entanglement as the web bonding process.

Further, it is provided for a sheet wherein the porous or absorbent substrate is a non-woven material obtained by subjecting at least one fibrous layer of non-woven fibers to carding by use of at least one carding unit to produce a precursor substrate in a web forming step which is subjected to hydro-entanglement.

Another embodiment of the invention provides for a sheet wherein the porous or absorbent substrate is a non-woven material obtained by subjecting at least one first fibrous layer of non-woven fibers to carding by use of at least one carding unit to produce a first pre-cursor substrate layer, placing at least one second fibrous layer onto the first precursor substrate layer by airlaying, subjecting at least one third fibrous layer of non-woven fibers to carding by use of at least one carding unit and placing said third precursor substrate layer-_adjacent to the second precursor substrate layer, furnishing a precursor substrate which is subjected to hydro-entanglement.

Of specific interest are sheets in accordance with the present invention which have been embossed with a wavelike pattern.

In still a further aspect there is provided a sheet in accordance with the present invention wherein the porous or absorbent material is a non-woven material, more in particular a non-woven material made by the spunlace or the hydro-entanglement procedure. Of particular interest are embodiments wherein the non-woven material is a spunlace material or a three-layer composite non-woven.

In still a further aspect, this invention provides a process for producing a porous or absorbent sheet as defined herein, said process comprising placing a web of fibres on or against a forming member having elevations and depressions and exerting an amount of pressure to press the web against the forming member, said amount of pressure being adequate to permanently emboss the sheet with the pattern of the forming member. The web may be entangled prior to, during or after the pressing of the web against the forming member. In a preferred execution, the web is pressed against the forming member under the influence of the pressure of the water jet during the hydro-entanglement.

In a preferred execution of this process the forming member comprises a bronze wire mesh on a support cylinder having raised and recessed regions shaped to form the raised and lowered regions on the sheet.

A pre-consolidated web is then pressed onto or respectively into the raised and recessed regions by hydrodynamic needling resulting in a wavy pattern on the non-woven.

The web that is pressed against the forming member may be loose or pre-consolidated to a more or less extent. The web may comprise fibre material pressed against an appropriately shaped forming mould.

The porous or absorbent sheet of the invention can be dry or can be impregnated and/or coated with a suitable composition. Particular compositions are aqueous liquids or oil-based liquids, particular of these comprising aqueous solutions, O/W emulsions, PIT emulsions, W/O emulsions, any kind of sprayable emulsions, multiple emulsions like W/O/W and O/W/O emulsions, Pickering emulsions, micro-emulsions, oil-based solutions or formulations and hydrodispersions.

The composition can be a water-based formulation, in particular an aqueous solution. The composition preferably is emulsion-based in which the emulsion can be water-in-oil or oil-in-water or can be of more complex nature such as water-in-oil-in-water. Preferably it is an oil-in-water emulsion, more preferably an oil-in-water emulsion prepared according to the phase inversion technique.

In still a further aspect there is provided the use of a product as described herein as a cleansing tool, in particular in personal care applications.

In another aspect the invention concerns the use of a product as described herein as an applicator of active substances.

In still another aspect the invention provides the use of a product as described herein as a combined cleanser and applicator of active substances.

DETAILED DESCRIPTION OF THE INVENTION

Whenever used in this description and claims, any percentage is weight by weight (w/w).

This present invention concerns a sheet as specified herein. A substantial portion of the substrate of which the sheet is made, either on one or both of the surfaces of the sheet, has a three dimensional pattern embossed therein. Substantial portion means that a major portion of the surface has a pattern embossed therein, for example more than about 50% of the surface has a pattern, in particular more than about 70%, or more than about 80%, further in particular more than about 90% of the surface has a pattern embossed therein. Preferably, the three dimensional pattern is present over the complete surface of the sheet. If partially embossed, the pattern may be present at one or more locations of the surface of the sheet, but preferably in that instance the embossed region forms one united region.

The embossed pattern may be present at one surface or at both surfaces of the sheet. Embodiments with one surface that is partially embossed or completely embossed and the second surface that is non-embossed, partially-embossed or completely embossed are meant to form part of this invention. Also comprised are embodiments where one or both of the surfaces of the sheet have two or more patterns of raised and lowered regions.

The sheets of the invention have a pattern comprising a series of raised and lowered regions, wherein none of the raised or lowered regions has any flat portion. The surface at the raised and lowered regions therefore is curved, no part thereof forms a flat surface. Neither the highest nor the lowest parts of the sheet's surface at the raised or lowered portions are flat. The basis weight of the substrate is about the same over the whole surface of the sheet, the term basis weight having its art-known meaning of weight per unit of surface. The density of the raised portions is lower than the density of the lowered portions, the term density equally having its art-known meaning of weight per unit of volume.

The height of the raised regions and the depth of the lowered regions may be equal or different. The height of the raised regions or the depth of the lowered regions may be the same all over the surface of the sheet, or the height of the raised regions or the depth of the lowered regions may differ. The height or depth of the raised or lowered regions at one surface may be different of that at the other surface. Preferably, the height of the raised regions is the same all over the surface of the sheet and/or the depth of the lowered regions is the same all over the surface of the sheet. More preferably, the height of the raised regions is equal to the depth of the lowered regions. As used herein, height of the raised regions refers to the distance between the highest point of the raised region to the point of the surface that is the average distance to the middle of the sheet. Equally, the depth of the lowered region is the distance between the lowest point of the lowered region to the point of the surface that is the average distance to the middle of the sheet. For example, where a transversal of the surface of the sheet forms a sinus or sinusoid, as outlined hereinafter, the sum of the depth and height defines the amplitude of the sinus or sinusoid.

The depth an height of the lowered and respectively raised regions preferably is in the range of 0.05 to 1 mm, more preferably in the range from 0.1 to 0.7 mm, still more preferably in the range of from 0.2 to 0.5 mm, further preferably from 0.2 to 0.4 mm, or about 0.3 mm. In the embodiments where a transversal of the surface of the sheet forms a sinus or sinusoid, as outlined hereinafter, the sum of the depth and height, i.e. the amplitude of the sinus or sinusoid preferably are in ranges which are about the double of the ranges mentioned above.

The thickness of the sheet at its thinnest portion, i.e. at the lowest point of the lowered regions may vary but preferably is in the range of 0.1 to 2 mm, more preferably from 0.2 to 1 mm, still more preferably from 0.3 to 0.7 mm, or about 0.5 mm. The thickness of the sheet at its thickest portion may equally vary and preferably is as the thickness of the sheet at its thinnest portion plus the depth and height of the lowered and raised portions as outlined herein.

Preferably, the density of the lowered regions is in the range of about 40 to 300, preferably of about 100 to 180 and most preferably of about 120 to 170 kg/m$^3$, and the density of the raised regions is in the range of about 20 to 120, preferably of about 50 to 100 and most preferably of about 60 to 90 kg/m$^3$.

In the embodiments where the raised and lowered regions form a pattern, one or more of such patterns may be present at one or at both surfaces of the sheet. If more patterns are present at one surface, one specific pattern is separated from the other, i.e. not running through one another. The different patterns may be adjacent or may be separated by areas that bear no pattern. Preferred are embodiments where one (one being of particular preference) or both of the surfaces of the sheet are completely covered by the pattern. The differences in the pattern may be various, they can reside in the shape of the raised and lowered regions, e.g. their general shape, or their width or length, the height of the raised areas or depth of the lowered areas, and the like. In the case of patterns which are lines or stripes as described here-below, lines or stripes of different width can be present.

In general, the distance between adjacent raised and lowered regions can also vary within one sheet as can the distance between consecutive raised regions.

In certain embodiments of this invention the lowered or raised regions are arranged in a pattern of recurring lowered and raised regions of about the same size. In specific embodiments of this invention, the shape of the raised and lowered regions is identical or about identical. As used herein, the terms about the same size or about identical shapes means that the size or shape is essentially the same, with small difference of e.g. less than 10% or less than 5%.

In still further specific embodiments, the raised and lowered regions form a linear pattern that runs in one direction continuously from one side of the sheet to the other side, especially the linear pattern runs in cross direction, e.g. the essentially linear raised and lowered regions are aligned in cross direction.

Preferably, the pattern of the lowered and raised regions runs in the machine direction by which the sheet is produced, that is the recurrent pattern of raised on lowered regions continues in the direction the substrate from which the sheet is obtained has been produced. In another embodiment, the pattern of raised and/or lowered regions runs in cross direction or in any other direction. In specific embodiments, the raised and lowered regions run in parallel.

The lowered and raised regions may also form a pattern of lines or stripes which can be straight or may be curved or broken. Lines or stripes that are not straight may run in a repetitive (or periodical) way such as in a sinus or sinusoid or sinusoid-like, in a zigzag and the like patterns. In case of a pattern of lines or stripes, and in particular if waving lines or stripes are selected, preferably the lines or stripes are in phase, so that parallelism is maintained and each stripe remains equally spaced from the adjacent lines or stripes.

The lines or stripes of raised and/or lowered regions can be continuous or discontinuous, either in a regular pattern or arbitrarily. If the lines or stripes have a wave-like pattern the amplitude of these waves and/or the length of these waves can be varied in broad ranges. Such alterations can take place on one or both sides of the absorbent sheet.

Examples of such patterns are those comprising a series of lowered and raised regions that follow a wave pattern, a zigzag pattern, or a pattern of multiple lines or stripes.

Of particular interest is a sheet in accordance with the invention which has been embossed with a wave-like pattern.

Of particular interest are embodiments wherein at least one of the surfaces of the sheet in a transversal section has a sinusoidal shape. Sinusoidal in this context means that the transversal section has a sinus-like shape, meaning that the surface section is curved and raises up and down in a repetitive way in more or less equal periods. Preferably, the surface section of a transversal section approximates a sinus, e.g. with more or less flattened sections (without becoming completely flat), or is a sinus.

In a cross-sectional view of the absorbent sheet a pattern can be chosen in one embodiment according to which the height and/or the depth of the raised and lowered regions, respectively, vary in an alternating fashion. For example, between two raised portions of the same height another raised portion having a lower height is arranged. Furthermore, the cross-section of a raised and/or lowered region can be symmetrical or unsymmetrical in shape. An unsymmetrical raised or lowered region can for example comprise two or more undulations. In another embodiment a recurrent pattern of raised and lowered regions can comprise a first raised region of larger height and a second and third raised regions being both of lower height whereas the width between the lowered regions of the first and second raised region is several times broader than the width between the lowered regions of the second and the third raised regions. Following the third raised region again a broad lowered region can follow. As is apparent from the above, the patterns of raised and lowered regions can be altered within a very broad range.

In further particular embodiments of this invention, the sheet in accordance with the invention has a pattern wherein the width of the lowered and of the raised regions is substantially the same over the whole surface of the sheet. In another aspect of the invention the width of a raised/or lowered region can also vary along its length. According to a further embodiment the width of the raised regions can be larger than that of the lowered or vice versa. The term "width" in this context refers to the distance between the point where the surface starts raising above the average height of the surface. The width may vary but in general is in the range of about 1 mm to 5 mm, in particular from about 2 mm to about 4 mm. A width of about 3 mm is of particular interest as it may provide products that are particularly effective in terms of softness and other beneficial properties.

Preferably, the width of the raised regions is about equal to that of the width of the lowered regions.

The absorbent or porous sheet can take the form of a tissue, a wipe, towel, towelette, and the like. The material may be flushable. As used herein, by 'flushable' is meant that the material will pass through at least 3 meters of waste pipe in two toilet flushes. The material may also be biodegradable which, for example, can be tested according to ASTM test method D 5209 also known as Sturm Test.

Materials of which the sheet is made may be mono or multi-layered, woven or non-woven. They can be made of one or of several materials. Particularly preferred are non-woven materials that have a web structure of fibrous or filamentous nature, in which the fibres or filaments are distributed randomly or with a certain degree of orientation, the former being obtainable by airlaying or certain wetlaying processes, the latter in certain other wetlaying processes or by drylaying, preferably_carding processes. The fibres or filaments can be natural, for example wood pulp, wool, cotton, linen and the like, natural man-made such as regenerated cellulose, e.g. viscose, modal, cupro, lyocell, cellulose acetate and the like, or synthetic, for example polyvinyls, polyesters, polyolefins, polyamides and the like.

It is preferred that the porous or absorbent substrate is a non-woven material, preferably a non-woven material obtained by carding, spunlaying, meltblowing, airlaying, wetlaying or a mixture thereof as the web forming process and by hydro-entanglement as the web bonding process.

In particular, the porous or absorbent substrate is a non-woven material made by spunlacing. With spunlacing a fibrous layer of non-woven fibers is subjected to carding by use of at least one carding unit to produce a precursor substrate in a web forming step which is then hydro-entangled for web bonding. Fibers suitable for spunlacing are, for example, regenerated cellulose fibers such as viscose, synthetic fibers such as polyester fibers, e.g. polyethylene terephthalate fibers (PET), or mixtures thereof. In another embodiment two, three, four or even more carded precursor webs are at least partially superimposed onto each other to form a sandwich structure which is subsequently subjected to the hydro-entanglement procedure. Depending on the intensity and duration of the hydro-entanglement procedure the individual layers are no longer discernible in the final spunlaced product. The individual fibrous layers can be made of the same or of different fibers or fiber blends.

In another aspect of the present invention the porous or absorbent substrate is a non-woven material made by airlacing. With airlacing at leat one first fibrous layer of non-woven fibers is subjected to carding by use of at least one carding unit to produce a first precursor substrate layer. Onto this first precursor substrate layer at least one second fibrous layer is placed by airlaying. Further, the second precursor substrate layer is at least partially covered by a third precursor substrate layer comprising at least one third fibrous layer of non-woven fibers having been subjected to carding by use of at least one carding unit. The aforementioned pre-cursor substrate layers when placed on top of each other form the precursor substrate which is subjected to hydro-entanglement furnishing a composite system wherein all layers are tightly bond to each other. In a particular execution, a first layer is formed which is by carding of staple fibre covering the thus formed layer with a second layer of pulp by airlaying, and in turn covering the pulp layer with a carded layer of staple. The thus obtained three layer structure is subsequently entangled, preferably by a hydro-entanglement process. Preferably, after laying each layer, the whole is calendered. Thus, in the aforementioned embodiment it is preferred that the non-woven material is derived from hydro-entangling a multi-layer, in particular a three-layer, composite non-woven, wherein in particular the intermediate layer has been obtained by airlaying. In a preferred embodiment, at least one, especially both, of the layers adjacent to the intermediate layer is/are made by use of carding.

According to another aspect of the present invention the precursor substrate is made by at least one first precursor substrate layer being made by at least one carding process as described above for the airlacing procedure and at least one second precursor substrate layer obtained by spunlaying placed at least partially on top of the first precursor substrate layer. Suitable fibers used for spunlaying are, for example, polypropylene, polyethylene, polyester, e.g. PET and PBT, and polylactide fibers or mixtures thereof. The aforementioned layered precursor substrate is then subjected to hydro-entanglement furnishing a composite system wherein all layers are tightly bond to each other In another aspect of the present invention to the aforementioned system of a first and second precursor substrate layer, i.e. adjacent to the spunlaid layer another carded, third precursor layer is placed prior to the hydro-entanglement web bonding step.

According to another aspect of the present invention the precursor substrate can advantageously also comprise at least one first precursor substrate layer made by use of at least one carding process as described above, and at least one second precursor substrate layer made by meltblowing. This precursor substrate is then subjected to the hydro-entanglement web bonding step.

Further, another preferred embodiment comprises at least one first precursor substrate layer made by use of at least one carding process as described above, at least one second precursor substrate layer made by meltblowing, and at least one third precursor substrate layer made by use of at least one carding process as described above and placed adjacent to the second pre-cursor substrate layer as the first layer to form the precursor substrate. This precursor substrate is then subjected to the hydro-entanglement web bonding step.

In another preferred embodiment the precursor substrate comprises at least one first pre-cursor substrate layer obtained by carding, e.g. as described above, followed by at least one second precursor substrate layer obtained by airlaying, e.g. as described above, followed by at least one third precursor substrate layer obtained by spunlaying, e.g. as described above, which in turn is followed by at least one fourth precursor substrate layer obtained by carding, e.g. as described above. These first to fourth precursor substrate layers when superimposed on top of each other form the precursor substrate which is then subjected to the hydro-entanglement procedure web bonding step.

In yet another embodiment of the present invention the precursor substrate comprises at least one first precursor substrate layer obtained by carding, e.g. as described above, followed by at least one second precursor substrate layer obtained by airlaying, e.g. as described above, followed by at least one third precursor substrate layer obtained by meltblowing, e.g. as described above, which in turn is followed by at least one fourth precursor substrate layer obtained by carding, e.g. as described above. These first to fourth precursor substrate layers when superimposed on top of each other form the precursor substrate which is then subjected to the hydro-entanglement procedure web bonding step.

For layers obtained by carding regenerated cellulose fibers, e.g. viscose, polypropylene, polyamide, polyester, e.g. polyethylene terephthalate, polylactide acid, polyvinyl alcohol fibers and/or natural fibers are particularly preferred.

It is in particular preferred that during web bonding by hydro-entanglement also the desired three-dimensional pattern is at least partially inparted onto the surface of the substrate.

Further, it is particularly preferred that the porous or absorbent substrate is a non-woven material made by airlacing and/or spunlacing.

Multi-layered sheet materials have two or more layers of the same or different materials, woven or non-woven, or layers obtained by different techniques. One embodiment is a material composed of three layers, e.g. polyethylene/pulp/polyethylene or viscose/polypropylene/viscose, (polypropylene+polyester)/pulp/(polypropylene+polyester), polypropylene/pulp/polypropylene.

Typically the sheets have a weight per square meter in the range of 10 to 80 g/m$^2$, in particular of 20 to 70 g/m$^2$. Particular materials are of the non-woven type. Based on the raw material that has been used, two different types of products can be distinguished.

A first type of carriers is paper based. The raw materials for these carriers are made almost exclusively of cellulose-based fibres or filaments from plant cellular sources (pulp). These can be available from fresh wood-shavings or from recycled material (recycled paper). In a number of wipe applications, such as baby wipes, wipes for cleansing, wet paper towels and the like, high wet strength or firmness of the non-woven web is a desirable attribute. This can be achieved by the addition of binding materials. Examples of such materials are the so-called wet strength resins. In some cases additives are added in order to increase the softness of the end product.

In a second type use the web is made mainly of staple fibre, e.g. based on cotton, wool, linen and the like, natural man-made such as regenerated cellulose, e.g. viscose, modal, cupro, lyocell, cellulose acetate and the like, or synthetic, for example polyvinyls, polyesters, polyolefins, polyamides and the like.

Commercial products are made of cellulose fibres, synthetic fibres or mixtures of both. Polyester and polypropylene are known as suitable polymers for the preparation of synthetic fibres. Also in these products binders can be used to increase the firmness of the non-woven fabric.

Webs of increased strength can be obtained by using the so-called spunlace or hydro-entanglement technique. In this technique the individual fibres are twisted together so that an acceptable strength or firmness is obtained without using binding materials. The advantage of the latter technique is the excellent softness of the non-woven material.

Non-woven materials that are made of a mixture of pulp and staple fibre are also known. Such materials are available with binding materials, in particular those mentioned above, or without binding materials. In the latter instance the non-woven is preferably made by the hydro-entanglement process, or more preferably by the spunlace process.

In one type of embodiments of the present invention, the sheet material is made of cellulose pulp with a small amount of binding material. The amount of binder in the sheet material is in the range of 5 to 20% (w/w).

In a preferred embodiment the non-woven sheet material is prepared by the water entanglement procedure and does not contain binding material.

A particular type of sheet materials are those made by entangling a bi-, tri-, or multi-layer material to a sandwich-structured material. Preferably the entanglement is done by hydro-entanglement. In particular embodiments, a three-layer web is entangled, preferably hydro-entangled. In preferred embodiments, the outer layers of the three-layer web are composed of staple fibre and the inner layer of a non-staple fibre material such as viscose, or, which is preferred, paper pulp. Suitable staple fibres are, for example, polyester, polypropylene or polyethylene, or mixtures thereof, the latter two being particularly preferred. Even more preferred are polyester and polypropylene. The layers of staple fibres may be of the same or different composition, e.g. composed of different staple fibres or of different mixtures of staple fibres. The outer layers of staple fibres may have the same thickness or same weight, or may be of different thickness or weight. Preferably, each outer layer comprises from 12.5-45% of the total weight of the end product and the middle layer comprises saying 10-75% of the total weight of the end product.

In a particularly preferred embodiment, the outer layers are composed of a mixture of polyethylene and polypropylene staple fibres, in particular from 10-90% of each of the components, but preferably in a 50/50% weight ratio. In an even more preferred embodiment, the outer layers are composed of a mixture of polypropylene and polyester staple fibres, in particular from 10-90% of each of the components, but preferably in a 50/50% weight ratio. Of particular interest is a three layer web composed of two outer layers of staple fibre as just described, each comprising about 25% of the weight of the end product and a pulp inner layer comprising 50% of the weight of the end product.

Each of the layers in the bi-, tri- or multi-layer sandwich web can be obtained by carding, airlaying, wetlaying, spun-laying or any combination thereof. Each layer can be formed by a different laying method, but preferably layers of the same composition are made by the same laying method.

In multi-layered systems which are prepared as outlined in the foregoing, in particular by use of the hydro-entanglement treatment, the individual layers can be indistinguishable thereby showing the coherent nature of the sheet according to the present invention.

In particularly preferred embodiments, the outer layers of the three-layered web, prior to the entanglement step, are contacted with a heated surface as described, for example, in US Patent Application 2003/0024092. A particular useful procedure comprises contacting the first carded staple fibre layer with a heated roll and subsequently the other carded staple fibre layer with another heated roll. Even more preferred, only the first, i.e. the lower carded staple fibre layer is contacted with a heated roll.

The sandwich web structure may be embossed during the entanglement procedure, more preferably during the hydro-entanglement procedure, or embossing may take place in a separate step, after entanglement. Or, the sandwich web structure may be consolidated by a first entanglement procedure and subsequently embossed and entangled in a combined step.

The absorbing ability of the sheet material is of particular interest with regard to the applications envisaged by the present invention. During production the impregnating solution should be taken up quickly by the sheet. In certain embodiments of this invention the wipes will be packed in a stack of a plurality of wipes. In this instance the absorbing ability of the non-woven fabric should be such that a chromatographic effect (sinking down of the lotion) in the stack is avoided during storage. On the other hand it should be guaranteed that during the usage of the wipe the impregnating solution is delivered evenly to the skin and the active ingredients are released quantitatively.

The absorbing capacity of the sheet material is determined essentially by three different parameters: the surface weight of the sheet material, the nature of the raw materials used in the manufacture and the manufacturing process used, and in particular the density of the sheet material.

For the applications according to the invention the sheet materials typically have a surface weight from 10 g/m² to 80 g/m², preferably from 30 to 70 g/m² and more preferably from 40 to 60 g/m². The selection of the raw materials of which the non-woven sheet material is made depends on the manufacturing procedure. Typically in the manufacture of non-woven sheets by the hydro-entanglement process, use is made of mixtures of cellulose fibres and synthetic fibres. The relative quantity of synthetic fibres in the non-woven fabric is from 0 to 100% and preferably is between 10 and 70%, more preferably in the range of 30 to 50% (all percentages being w/w).

The porous or absorbent sheet subject of this invention can be made by a process that comprises placing a web of fibres on or against an appropriately shaped forming member having elevations and depressions. Depending on the production set up, the web can be placed on the forming member or vice versa the forming member can be placed on the web. The forming member a roll or drum or part of a roll or drum, e.g. the member can be curved and can be mounted on a roll or drum.

The forming member, also called forming sleeve or sleeve, can for example be a forming plate or a woven wire screen such as a wire mesh. In particular, the forming member comprises a forming plate, a forming belt and/or a forming cylinder.

The web may be loose, or consolidated to a less or more extent, e.g. the web may be pre-consolidated or partially consolidated. The web may even be partially or completely entangled. The forming member can be planar or can be curved. Preferably it is circular and is mounted as a sleeve on a roll or drum which forms part of the production line. The forming member can be made of any material of suitable strength, e.g. synthetic or metal.

In a preferred embodiment the forming member at least on one of its surfaces is made at least partially from metal, in particular steel, copper and/or bronze, or synthetic material, in particular plastic such as polyolefins, e.g. polypropylene and polyethylene, polyamides, poly(meth)acrylates, e.g. polymethylmethacrylate, polyester, e.g. polyethylene terephthalate and polybutylene terephthalate, polystyrene, styrene-copolymers, e.g. ASA, ABS and SAN, polyacetals, e.g. polyoxymethylene (POM), polyphenylene ether (PPE), polyvinyl chloride, polyurethanes, or polytetrafluoroethylene (Teflon®), synthetic rubber and/or thermoplastic elastomers (TPE), and/or natural rubber. The aforementioned plastic materials also include mixtures of the polymers mentioned, e.g. PPE/ABS, PPE/SAN, PPE/ASA and/or impact modified variants of the polymeric materials mentioned.

Further, in one embodiment it is preferred that the forming member comprises an essentially continuous surface which comprises said elevations and depressions. Such a forming member can for example comprise a so-called seamless, endless sleeve. With such a continuous surface the elevations or raised portions and recesses, depressions or lowered portions of the forming member in general are not provided with holes or are not of a foraminous nature. However, such a continuous surface can have at least one downspout so that the water being used during the hydro-entanglement process can drain away. The aforementioned forming member allows for increased line efficiency, reduces the necessary cleaning times and cycles, and is usually cheaper than forming members being perforated or being prepared from wired mesh.

In general, the pattern of elevations/raised portions and depression/lowered portions of the forming member are obtained by known engraving techniques such as Laser engraving. These elevations and depressions essentially mirror the lowered and raised regions of the sheet of the invention, respectively. If, for example, the raised portions/elevations of the forming member are flattened at their top parts this will usually result in lowered regions of the sheet material having a flattened bottom part.

By use of flattened raised portions/elevations in the forming member a very tight sheet material is obtained which is still superior in softness. Also, the hydro-entanglement process furnishes a very coherent sheet not showing any holes or apertures.

For the manufacture of lowered regions having flattened bottom parts preferably forming members formed from a synthetic material, preferably of polymeric material, in particular from poly(meth)acrylates, polyacetals, polyesters, polyamides and/or polytetrafluoroethylene, are employed.

Also, preferably, the forming member is a woven screen comprising a mesh of wire of suitable strength. The wires in the mesh can be made of metal or synthetic, e.g. of a plastic material, or both. Suitable metals are steel, copper, or which is preferred bronze.

In a preferred execution of this process the forming member comprises a bronze wire mesh on a support cylinder having raised and recessed regions shaped to form the raised and lowered regions on the sheet.

It is particularly preferred that if a forming member, e.g. a forming cylinder or a forming belt, is placed onto a support member the forming member is fixedly attached to the support member. In this way there is no relative movement between the forming member and the support member. In one embodiment of a forming member being fixedly attached to a support member there is no or essentially no clearance between the forming member and the support member. Under the aforementioned prerequisites the forming member does not move freely on the support member. In another embodiment where there is a clearance between the forming member and the support member the forming member is not fixedly attached to the support member thereby furnishing a forming member which is at least to a limited extent movable on the support member.

According to another aspect of the invention the forming member is a self-sustaining forming member having the advantage that no additional support member, e.g. a support cylinder, is needed.

The embossing step comprises exerting an amount of pressure to press the web on or against the forming member, said amount of pressure being adequate to permanently emboss the sheet with the pattern of the forming member. In the embossing step, the web is pressed onto or respectively into the raised and recessed regions resulting in a pattern in the sheet material. The web may be entangled prior to, during or after the pressing of the web against the forming member. In a preferred execution, the embossing takes place in combination with an entanglement step, which may be partial or complete entanglement. Particularly preferred in this step is hydro-entanglement in which the web is pressed against the forming member under the influence of the pressure of the water jet of the hydrodynamic needling during the hydro-entanglement procedure. In the latter instance, the forming member is perforated to allow the water of the water jets to become removed. A particular useful forming member in this instance is the above mentioned forming member of mesh wire. In a particularly attractive execution, the web, which preferably is pre-consolidated spunlace, is during the embossing step pressed onto or respectively into the raised and recessed regions, by hydrodynamic needling during which a further hydro-entanglement step takes place.

The embossing step preferably takes place at the end of the production process of the sheet material.

The sheets according to the invention offer the advantage that they allow for an easier and more evenly distribution of skin care compositions or ingredients in or on the product. They moreover can absorb soilage and make-up very efficiently, and offer a very soft sensation to the skin. Without being bound by theory it is believed that with the sheets of the invention the effective contact area between sheet and skin is reduced. It has been found that such a reduced contact area alleviates skin cleansing properties and that also any skin care compositions having been impregnated into the sheet can be evenly and sufficiently delivered via the surface structure of the sheet of the invention.

The sheets according to the invention may be used as dry or essentially dry products or they may be loaded with suitable compositions. As used herein, the term dry means that the sheet products contain no or limited amounts of water, e.g. less than 1% and essentially dry means that the sheet contains limited amounts of water, e.g. less than 10% of the total weight of the sheet, preferably less than 8%, more preferably less than 5%, still more preferably less than 2% of the total weight of the sheet. These compositions can be any compositions known in the art with which sheets are loaded. The compositions can be liquid, semi-solid or solid and the sheet can be loaded with one or more different compositions. In a particular embodiment, the composition is a liquid. It can be coated onto or impregnated into said sheet.

The sheet can be impregnated with different kinds of lotions, among these are aqueous liquids, aqueous lotions, emulsions such as w/o emulsions, O/W emulsions or multiple emulsions like W/O/W and O/W/O emulsions, Pickering emulsions, sprayable emulsions, microemulsions, PIT emulsions, hydrodispersions and also oily formulations.

Compositions

Of particular interest are compositions that are liquid compositions. They can be water-based formulations, in particular they can take the form of aqueous solutions. The liquids preferably are emulsion-based. These liquid compositions, which also are referred to as 'lotions', preferably are of aqueous nature.

Aqueous Solutions

A first group of compositions that can be applied to the sheets are the so-called 'aqueous solutions'. These in particular comprise aqueous based compositions that are not emulsions, or do not contain emulsions, or contain only small amounts of emulsions. Small amounts in this context mean less than about 10%, in particular less than 5%, more in particular less than 3% or less than 1%, w/w expressed in relation to the total weight of the composition.

The aqueous solutions may contain further ingredients, in particular the further ingredients mentioned herein. A particular sub-type of aqueous solutions is for cleansing, i.e. so called 'cleansing lotions'. The latter contain specific cleansing agents such as surfactants and optional further components such as emollients, fragrances, preservatives, actives and the like. Small amounts of solubilizers may be added to solubilize oily components, e.g. oily fragants or oily actives. Of specific interest are the betaine surfactants. Specific emollients are polyalcohols such as glycerine, ethylene, glycol, propylene glycol and the like.

Emulsions

Preferably the compositions are emulsion-based. The emulsions can be oil-in-water or water-in-oil emulsions, or be of more complex nature such as water-in-oil-in-water. Preferred are oil-in-water emulsions.

The compositions in the products of the invention may further contain one or more emulsifiers which can be of the W/O or the O/W type.

Preferred are non-ionic emulsifiers which typically have good skin compatibility. Improved sensoric properties are obtained when combining non-ionic W/O and O/W emulsifiers. The compositions may contain the emulsifier(s) in an amount of 0 to 20% (w/w), respectively 0.1 to 15% (w/w) and in particular 0.1 to 10% (w/w) relative to the total quantity of the compositions.

Particular non-ionic emulsifiers comprise:

Addition products of 2 to 50 moles of ethylene oxide and/or 0 to 20 moles propylene oxide to linear fatty alcohols having 8 to 40 C-atoms, to fatty acids with 12 to 40 C-atoms and to alkylphenols with 8 to 15 C-atoms in the alkyl rest.

$C_{12/18}$-fatty acid mono- and -diesters of addition products of 1 to 50 moles of ethylene oxide and glycerine.

Glycerine mono- and -diesters and sorbitan mono- and -diesters of saturated and unsaturated fatty acids with 6 to 22 C-atoms and their ethylene oxide addition products.

Alkyl mono- and -oligoglycosides with 8 to 22 C-atoms in the alkyl rest and their ethoxylated analogs.

Addition products of 7 to 60 moles of ethylene oxide to castor oil and/or hardened castor oil. Polyol- and in particular polyglycerine esters, such as e.g. polyol poly-12-hydroxystearate, polyglycerine polyricinoleate, polyglycerine diisostearate or polyglycerine dimerate. Also applicable are mixtures of compounds of several of these substance classes.

Addition products of 2 to 15 moles of ethylene oxide to castor oil and/or hardened castor oil. Partial esters derived from linear, branch chained, unsaturated or saturated $C_6$-$C_{22}$-fatty acids, ricinoleic acid as well as 12-hydroxystearic acid and glycerine, polyglycerine, pentaerythrite, dipentaerythrit, sugar alcohols (e.g. sorbitol), alkylglucosides (e.g. methylglucoside, butylglucoside, laurylglucoside) as well as polyglucosides (e.g. cellulose), or mixed esters such as e.g. glyceryl stearate/citrate and glyceryl stearate/lactate.

Wool wax alcohols.

Polysiloxane-polyalkyl-polyether-copolymers and derivatives thereof.

Mixed esters from pentaerythrite, fatty acids, citric acid and fatty alcohols and/or mixed esters of fatty acids with 6 to 22 C-atoms with methylglucose and polyoles, respectively glycerine or polyglycerine.

Polyalkylene glycols.

The addition products of ethylene oxide and/or of propylene oxide and fatty alcohols, fatty acids, alkylphenols, glycerine mono- and -diesters as well as sorbitan mono- and -diesters of fatty acids or of castor oil are known and commercially available products. Usually these are mixtures of homologues of which the average degree of alkoxylation corresponds to the ratio of starting quantities of ethylene oxide and/or propylene oxide and substrate, with which the addition reaction is conducted. Depending upon the degree of alkoxylation these products are either W/O- or O/W-emulsifiers. $C_{12/18}$-fatty acid mono- and -diesters of addition products of ethylene oxide to glycerine are known as re-fatting agents in cosmetic applications.

Particular useful and mild emulsifiers are polyolpoly-12-hydroxystearates and mixtures thereof with other components, that are available under the tradename "Dehymuls® PGPH" (W/O-emulsifier) or "Eumulgin® VL 75" (1:1 w/w mixture with coco-glucosides, O/Wemulsifier) or Dehymuls® SBL (W/O-Emulsifier) from Cognis Deutschland GmbH. The polyol components of these emulsifiers can be derived from materials that have at least two and in particular 3 to 12 and more in particular 3 to 8 hydroxyl groups, and 2 to 12 carbon atoms.

An emulsifier which is can be added is selected from the group of non-ionic O/W-emulsifiers (HLB-value: 8-18) and/ or solubilizers. These can for example be the already mentioned ethylene oxide-adducts with a corresponding high degree of ethoxylation e.g. 10-20 ethylene oxide units in the case of O/W-emulsifiers and 20-40 ethylene oxide units for so-called solubilizers. Particularly attractive as O/W emulsifiers are Ceteareth-12 and PEG-20 stearate. Particularly attractive solubilizers are Eumulgin® HRE 40 (INCI: PEG-40 Hydrogenated Castor Oil), Eumulgin® HRE 60 (INCI: PEG-60 Hydrogenated Castor Oil), Eumulgin® L (INCI: PPG-1-PEG-9 Laurylglycolether) and Eumulgin® SML 20 (INCI: Polysorbate-20).

Non-ionic emulsifiers of the group of alkyl oligoglycoside are particularly skin-compatible and therefore preferred as O/W-Emulsifiers. $C_8$-$C_{22}$-alkyl mono- and -oligoglycosides, their preparation and use have been described in the prior art. Oligoglycosides are meant to comprise oligomeric glycosides with a degree of oligomerisation of up to about 8. The degree of oligerisation can also be a statistical average used for those products comprised of a specific range of oligoglycosides. An example is the product sold under the tradename Plantacare® which has a $C_8$-$C_{16}$-alkyl group glycosidically bound to an oligoglucoside rest, having an average degree of oligomerisation between 1 and 2.

Other non-ionic emulsifiers are the acyl glucamides. Preferred is the product sold under the tradename Emulgade® PL 68/50 (Cognis Deutschland GmbH) which is a 1:1-mixture of alkyl polyglucosides and fatty alcohols, and a mixture of lauryl glucoside, polyglyceryl-2-dipolyhydroxystearate, glycerine and water, sold under the trade name Eumulgin® VL 75.

Lipophilic W/O-emulsifiers in principle are emulsifiers with a HLB-value in the range of 1 to 8, that are described, for example, in Kirk-Othmer, "Encyclopedia of Chemical Technology", $3^{rd}$ Ed., 1979, Vol. 8, p. 913. The HLB-value of ethoxylated products is calculated by the formula: HLB= (100-L): 5, wherein L is the percentage (in weight %) of lipophilic groups, i.e. of fatty alkyl- or fatty acyl groups in the ethylene oxide adducts.

Particularly attractive W/O-emulsifiers are the partial esters of polyoles, in particular of mono-, di- or tri-, sesqui esters of fatty acids of polyoles, more in particular of $C_3$-$C_6$-polyoles, such as, for example, glyceryl monoesters, partial esters of pentaerythrite or carbohydrate esters, e.g. saccharose distearate, or sorbitane mono-, di-, tri- or sesqui fatty esters in particular stearates, oleates, erucates, ricinoleates, hydroxystearates, isostearates (but also: tartrates, citrates, maleates) and the like. Also attractive are addition products of 1 to 30, respectively 5 to 10 moles ethylene oxide to these sorbitane esters.

Preferred compositions are those based on emulsions prepared by the so-called phase inversion technique.

According to this technique, oil-in-water formulations made with non-ionic emulsifiers typically undergo a phase inversion upon heating which means that within a particular temperature interval a change of the emulsion type takes place, i.e. from an oil-in-water to a water-in-oil emulsion. In this process the external continuous phase changes from being aqueous to an oily phase resulting in a drop of the electrical conductivity to virtually zero. The average temperature between that of maximal and of minimal conductivity is referred to as the phase inversion temperature ('PIT').

After heating to a temperature above the PIT, the emulsion is cooled below the PIT whereupon the inverse phase transfer takes place, i.e. from water-in-oil to oil-in-water. The resulting emulsions are usually referred to as 'PIT emulsions'.

The droplet size of the PIT emulsion depends on a number of factors. PIT emulsions with small droplet size can be obtained with emulsions forming micro-emulsions having a low surface tension between the oil and water phases at the phase inversion, or that form a laminar liquid crystalline phase.

Preferred are PIT emulsions that are finely dispersed, i.e. having a small droplet size and have low viscosity.

The oily phase in PIT emulsions comprises natural oils or natural oil derivatives, in particular of vegetal origin. Examples are linseed oil, palm oil, olive oil, castor oil, rapeseed oil, soja oil, and in particular peanut oil, coconut oil, sunflower oil and turnip seed oil. The oily phase may further comprise fatty components isolated from these natural oils, i.e. pure triglycerides or mixtures thereof, or the latter components having been prepared chemically. These so-called trigycerides are esters of glycerine with fatty acids or fatty acid mixtures. Preferred triglycerides are those glycerine esters derived from fatty acids, either saturated or unsaturated, having from 10 to 24, particularly from 14 to 20, preferably from 16 to 18 carbon atoms, for example palmitic, heptadecanoic, oleic or stearic acid, or mixtures thereof. Particularly preferred is glyceryl stearate, also referred to as stearin.

The oily phase may further comprise alkyl esters of fatty acids, wherein the alkyl group has from 1 to 4 carbon atoms. Preferred are $C_{1-4}$ alkyl esters of $C_{16-18}$ fatty acids, for example of palmitic, heptadecanoic, or stearic acid, in particular the methyl or ethyl esters, including mixtures thereof.

Of particular interest are oily phases that comprise a vegetable oil or a triglyceride in combination with an alkyl ester of a fatty acid.

The PIT emulsion further contains a non-ionic emulsifier.

Suitable non-ionic emulsifiers comprise:

polyethoxylated or propoxylated fatty alcohols, fatty acids or $C_{8-15}$ alkylphenols, having 2 to 30 ethoxy units and 0 to 5 propoxy units, or 1 to 5 propoxy units, prepared by reacting the starting alcohols with ethylene or propylene oxide;

mono- or diesters of polyethoxylated glycerine that with saturated or unsaturated $C_{12-18}$ fatty acids, having 1 to 30 ethoxy units;

glycerin mono- or diesters and sorbitan mono- or diesters of saturated or unsaturated fatty acids as well as ethoxylated derivatives thereof, the latter in particular having from 1 to 30 ethoxy units;

$C_{8-22}$ alkyl mono- or oligoglucosides as well as ethoxylated derivatives thereof, the latter in particular having from 1 to 30 ethoxy units;

ethoxylated castor oil or hydrogenated castor oil, in particular having from 1 to 30 ethoxy units;

polyol fatty acid esters and in particular polyglycerine fatty acid esters, more in particular ricinoelic acid or hydroxy stearic acid esters; for example polyglycerine poly ricinoleic acid or polyglycerine poly 12-hydroxystearate; and mixtures thereof;

glycerine, polyglycerine, mono- and di-pentaerythrite, sugar derived alcohols such as sorbitol, alkylglucosides and polyglucosides, partially esterified with one or more fatty acids or fatty acid mixtures;

trialkylphosphates as well as polyethoxylated derivatives thereof, the latter in particular having from 1 to 30 ethoxy units;

wool wax alcohols;

polysiloxane-polyalkyl-polyether copolymers and derivatives thereof;

mixed ethers of pentaerythrite, fatty acids, citric acid and fatty alcohols polyalkylene glycols;

glycerine carbonate.

As used herein the term fatty acid refers to saturated or unsaturated, straight or branch chained alkanoic acids, optionally substituted with one or more hydroxy groups.

Particular useful emulsifiers comprise an emulsifier system containing a mixture of a hydrophilic and hydrophobic emulsifier.

Hydrophilic emulsifiers comprise ethoxylated fatty alcohols or fatty acids. Examples of the former are ethoxylated $C_{16-22}$ alcohols such as for example cetyl, palmoleyl, stearyl, isostearyl and oleyl alcohol and mixtures thereof wherein the number of ethoxyl groups per molecule is in the range of 1 to 35, preferably from 1 to 20, more preferably from 10 to 20.

Examples of ethoxylated fatty acids are ethoxylated $C_{12-22}$ alkylcarbonic acids such as, for example, palmitinic, palmoleinic, steraic, isosearic acid and mixtures thereof, wherein the number of ethoxy groups is in the range of 5 to 50, in particular from 15 to 35.

Hydrophobic emulsifiers comprise polyethoxylated glycerin fatty acid mono- and diesters having 1 to 30 ethoxy units, i.e. polethoxylated glycerin wherein between 1 and 2 of the hydroxy functions have been esterified with 1 or 2 fatty acids or fatty acid mixtures.

The w/w ratio of the hydrophilic emulsifier components to the hydrophobic emulsifier components is in the range of 10:90 to 90:10, in particular 25:75 to 75:25, more in particular in the range of 40:60 to 60:40.

The PIT emulsions for use in the products according to the invention in particular contain from 20 to 90%, more in particular from 30 to 80% and preferably 30 to 60% of water. The remainder making up the formulation comprises the oily phase, the emulsifiers and other components. The oily phase typically comprises from 10 to 80%, in particular from 40 to 70% of the formulation. Preferred are emulsion wherein the w/w ratio of the oil and compositions are about 1:1. The emulsifiers are present in an amount that is in the range of 1 to 25%, in particular 5 to 20% and more in particular 5 to 15%.

The phase inversion temperature typically is in the range from 20 to 95° C., in particular in the range from 40 to 95° C.

The PIT lotions for use in the present invention will contain one or more light absorbing or light reflecting substances in particular those mentioned herein. These can be hydrophilic or hydrophobic. In the former instance these substances will be solved into the compositions while in the latter into the oily phase.

Particular PIT emulsions that can be used in the compositions of this invention are described for example in WO-00/51427 and in WO-00/71676

The compositions prepared by the phase inversion technique preferably have a viscosity of below 100 mPas. The average particle size of the oil droplets is in the range of 50 to 300 nm, in particular in the range of 50 to 200 nm, and preferably is 100 nm or smaller, e.g. between 70 and 90 nm. These compositions are particularly attractive in that they show good spreading and impregnating properties.

Other Components

The compositions may also contain further ingredients or additives such as surfactants, consistency factors, conditioners, moisturizers, thickeners, preservatives, active ingredients, in particular dermatologically active ingredients, fragrances, film forming agents, UV-filters, anti-oxidants, hydrotropic agents, preservatives, insect repellents, self-tanning agents, solubilizers, perfume oils, dyestuffs and the like.

Suitable anti-oxidants are agents that block oxidation or autoxidation of the components in the compositions for use in or on the sheet products of the invention. Examples of anti-oxidants are e.g. sulfites, e.g. sodium sulfite, tocopherol or derivates thereof, viatmine E or derivatives thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenoles, tocopherol, butylhydroxytolunene (BHT), butylhydroxyannisol (BHA), lecitine, and the like.

The emollients that may be added comprise lipids like lanolin, lanolin alcohols, lanolin acids, polyethoxylated or acylated lanolin or lanolin derivatives, lecithin and lecithin derivatives, fatty alcohols, either linear or branched with chain lengths between C6 and C40, and their esters with organic acids, e.g. carbonic acids or polyacids containing between 2 and 30 C atoms, branched, aromatic or linear including hydroxy or amino acids, fatty acids and fatty acid esters with alcohols or poly alcohols containing between 2 and 40 C atoms, branched, aromatic or linear, sterols found in the unsaponifiable fraction of e.g. avocado oil, almond oil, soybean oil, etc. like soy phytosterol, β-sitosterol, β-sitosteryl laurate, β-sitosteryl stearate, etc. natural and synthetic waxes, e.g. bees wax, purcelline, shea butter, cocoa butter, ceresin, ozokerit, vaseline, micro wax, carnauba wax candelilla wax and alike, substituted cyclohexanes like di-n-octylcyclohexane, Guerbet carbonates, e.g. bis-2-octyl dodecylcarbonate, dialkyl ethers like di-n-octyl ether, and the like:

Examples of oils are natural oils, e.g. almond oil, soybean oil, wheat germ oil, avocado oil, jojoba oil, linseed oil, sesame oil, walnut oil, sunflower oil, olive oil, etc., mineral and paraffin oil and synthetic oils comprising mono-, di-, triglycerides as well as mixtures thereof.

The compositions may also contain film-forming substances like chitosan and derivatives thereof, derivatives of poly acrylic acid, polyvinyl pyrrolidone and its derivatives, and the like.

Substances that can be used as superfatting agents are, for example, lanolin or lanolin derivatives such as lanolin alcohols, lanolin acids, polyethoxylated or acylated lanolin, or other lanolin derivatives; phospholipids such as lecithin or lecithin derivatives such as polyethoxylated or acylated lecithin or other lecithin derivatives; polyol fatty acid esters, monoglycerides and fatty acid alkanolamides.

Appropriate thickeners for example are of the Aerosil®-type (hydrophilic silica acids), polysaccharides, in particular xanthan-gum, guar-guar, agar-agar, alginate and tyloses, carboxymethyl cellulose and hydroxyethyl cellulose, additionally relatively high molecular weight polyethylene glycol mono- and -diesters of fatty acids, polyacrylate, (for example Carbopol® of Goodrich or Synthalene® of Sigma), polyacrylamides, polyvinylalcohol and polyvinylpyrrolidone, surfactants such as, for example, ethoxylated fatty acid glycerides, ester of fatty acids with polyoles such as, for example, pentaerythrit or trimethylolpropane, fatty alcohol ethoxylates having limited range of homologs or alkyloligoglucosides as well as electrolytes such as sodium chloride ammonium chloride.

Appropriate cationic polymers are for example cationic cellulose derivatives, e.g. quaternized hydroxyethyl cellulose (commercialized under the trade name Polymer JR 400® by Amerchol), cationic starches, copolymers of diallylammonium salts and acrylamides, quaternized vinylpyrrolidone/vinylimidazole-polymers (for example Luviquat® of BASF), condensation products of polyglycols and amines, quaternized collagen polypeptides, such as, for example, lauryldimonium hydroxy-propyl hydrolyzed collagen (Lamequat®L/Grtinau), quaternized wheat polypeptides, polyethylene imines, cationic silicone polymers, e.g. amodimethicone, copolymers of adipinic acid and dimethylaminohydroxypropyldiethylenetriamine (Cartaretine®/Sandoz), copolymers of acryl acid with dimethyldiallylammoniumchloride (Merquat® 550/Chemviron), polyaminopolyamides, cationic chitine derivatives such as, for example, quaternized chitosans, optionally dispersed in microcristalline form, condensation products derived from dihalogenalkylenes, such as, for example dibromobutane with bisdialkylamines, e.g. bis-dimethylamino-1,3-propane, cationic guar-gum, such as, for example, Jaguar® CBS, Jaguar® C-17, Jaguar® C-16 from Celanese, quaternized ammonium saltpolymers, e.g. Miapol® A-15, Mirapol® AD-1, Mirapol® AZ-1 from Miranol.

Anionic, zwitterionic, amphoteric and nonionic polymers that can be used are, for example, vinylacetate/crotonic acid-copolymers, vinylpyrrolidon/vinylacrylate-copolymers, vinylacetate/butylmaleate/isobornylacrylate-copolymers, methylvinylether/maleic acid anhydridecopolymers and their esters, which are not cross-linked and with polyoles linked polyacrylacids which are cross-linked, acrylamidopropyl trimethylammonium chloride/acrylatecopolymers, octylacrylamide/methylmethacrylate/tert.butylaminoethylmethacrylate/2-hydroxypropylmethacrylate-copolymers, polyvinylpyrrolidone, vinylpyrrolidone/vinylacetate-copolymers, vinylpyrrolidone/dimethylaminoethylmethacrylate/vinyl caprolactam-terpolymers as well as optionally derivatized cellulose ethers and silicones.

As further consistency agents there can be used small amounts of alkalimetal or alkaline earth metal as well as aluminium salts of $C_{12}$-$C_{24}$-fatty acids or $C_{12}$-$C_{24}$-hydroxy-fatty acids, preferred being calcium-, magnesium-, aluminium- and in particular zinc stearates.

The compositions may further contain powders or powdered ingredients or mixtures thereof such as talcum, Bolus alba, myristyl alcohol, cetyl alcohol, cetylstearyl alcohol, calcium or magnesium stearate, magnesium lauryl sulfate, starch or derivatives thereof e.g. distarch phosphate, aluminium starch octenylsuccinate, carboxymethyl starch, tapioca starch, dimethylimidazolidinone rice starch, sodium starch glycolate, potato starch, rice starch, corn starch, hydroxypropyl starch, hydroxyethyl starch and the like.

The compositions may further contain one or more preservatives such as, for example, phenoxyethanol, $C_{1-4}$ alkylparabens and their salts, in particular their alkali metal salts such as sodium salts (e.g. $C_{1-6}$ alkyl parabens such as methyl, ethyl, propyl, isopropyl, butyl paraben and the like parabens), chlorohexidine, formaldehyde or formaldehyde releaser, benzyl alcohol, chloroxylenol, phenoxyethanol, methylchloroisothiazolinone, methylisothiazolinone, sodium benzoate, chlorohexidine digluconate methyldibromo glutaronitrile, sodium-borate, 5-bromo-5-nitro-1,3-dioxane, alcohol, benzoic acid, dehydroacetic acid, diazolidinyl urea, dichlorobenzyl alcohol, glucose oxidease, hexamidine diisethionate, imidazolidinyl urea, iodopropynyl butylcarbamate, isobutylparaben, isopropylparaben, lactoperoxidease, magnesium nitrate, PEG-4 laurate, phenethyl alcohol, polyaminopropyl biguanide, potassium sorbate, propylene glycol, pyridoxine HCl, quaternium-15, sorbic acid, triclosan, tocopherol and the like.

Surfactants/Emulsifiers

Depending upon the use of the products of the present invention, the compositions may further contain zwitterionic, amphoteric, cationic and or anionic surfactants that may also function as emulsifiers.

Zwitterionic surfactants are those surface active compounds, that contain at least a quaternary ammonium group and at least a —$COO^{(-)}$— or —$SO_3^{(-)}$— group. Particularly useful zwitterionic surfactants are the so-called betaines such as N-alkyl-N,N-dimethyl ammonium glycinate, for example coco-alkyl dimethylammonium glycinate, N-acyl-aminopropyl-N,N-dimethylammonium glycinate, for example cocoacyl aminopropyl dimethylammonium glycinate, and 2-alkyl-3-carboxylmethyl-3-hydroxyethylimidazoline, each having 8 to 18 C-atoms in the alkyl- or acyl group as well as coco-acyl amino ethyl hydroxyethyl carboxymethyl glycinate. A preferred zwitterionic surfactant is the fatty acid amide-derivative known by its INCI-name cocamidopropyl betaine.

Amphoteric surfactants can further be added, in particular as co-surfactants and comprise those surface active compounds, that beside a $C_8$-$C_{18}$-alkyl- or acyl group at least contain a free amino group and at least a —COOH— or —$SO_3H$— group and are able to form internal salts. Examples of appropriate ampholytic surfactants are N-alkyl glycines, N-alkyl propionic acids such as N-coco-alkyl aminopropionate, N-alkyl amino buteric acids, N-alkyl iminodipropionic acids, N-hydroxyethyl-N-alkyl amidopropyl glycines, N-alkyl taurine, N-alkyl sarcosine, 2-alkylaminopropionic acids and alkylamino acetic acids with in each alkyl group about 8 to 18 C-atoms. Suitable amphoterics comprise, e.g., cocamidopropyl betaine, sodium cocoamphoacetate, sodium lauroamphoacetate, disodium lauroamphodiacetate, disodium cocoamphodiacetate, sodium lauroamphopropionate, disodium lauroamphodipropionate, potassium or ammonium salts of the aforementioned amphoterics, capryl/capramidopropyl betaine, undecyleneamidopropyl betaine, lauramidopropyl betaine.

Anionic surfactants are characterized by a water solubilizing anionic group such as a carboxylate-, sulfate-, sulfonate- or phosphate-group and a lipophilic rest. Particular anionic surfactants are the alkali-, ammonium- or alkanol ammonium salts of alkyl sulfates e.g. sodium lauryl sulfate, -ammonium lauryl sulfate, sodium cetearyl sulfate alkyl ethersulfates, e.g. sodium laureth sulfate, sodium trideceth sulfate, sodium oleth sulfate, ammonium laureth sulfate, alkyl ethercarboxylates alkyl sulfoacetates, e.g. sodium lauryl sulfoacetate; acyl isethionates, alkyl ether sulfosuccinates, e.g. disodium laureth sulfosuccinate, acyl sarcosinates, acyl taurines with linear alkyl- or acyl groups having 12 to 18 C-atoms as well as alkali- or ammonium salts of sulfosuccinates and acyl glutamates.

Quaternary ammonium derivatives can in particular be used as cationic surfactants. Preferred are ammonium halogenides, in particular chlorides and bromides, e.g. alkyl trimethylammonium chloride, dialkyl dimethylammonium chloride and trialkyl methylammonium chloride, z. B. cetyl trimethylammonium chloride, stearyl trimethylammonium chloride, distearyl dimethylammoniurnm chloride, lauryl dimethylammonium chloride, lauryl dimethylbenzylammonium chloride and tricetyl methylammonium chloride. Additional cationic surfactants are the quaternary esters with good biological degradability, such as, for example, dialkylammonium methosulfates and methylhydroxyalkyl dialkoyloxy alkylammonium methosulfates (sold under the tradename Stepantex® and the products of the Dehyquart®-series). The term "Esterquats" is meant to comprise quaternized fatty acid triethanolamine ester salts which have a beneficial impact on the softness of the phases, in particular of the composition. Further cationic surfactants are the quaternized protein hydrolysates. Non-ionic surfactants comprise alkyl glucosides, e.g. decyl glucoside, lauryl glucoside; alkyl isothionates;

Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, agents selected from glyceryl monooleate and cocoglucoside including mixtures thereof (in particular the product 'Lamesoft®' of Cognis which is a mixture of these two components), quaternized protein hydrolysates, quaternized cellulose and starch derivatives, quaternized copolymers of acrylic or methacrylic acid or salts, quaternized silicone derivatives, silicone oils, cyclomethicones, and the like agents, including mixtures thereof.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylene/ethylene/styrene copolymer.

The compositions may further comprise film-forming substances like chitosan and derivatives thereof, derivatives of poly acrylic acid, polyvinyl pyrrolidone and its derivatives, and the like.

Softeners

Of particular interest are those products of the present invention, that further comprise a composition containing a $C_{12-30}$ carboxylic acid glyceride, or further in particular a combination of a $C_{12-30}$ carboxylic acid mono- or diglyceride and a $C_{8-20}$ alkyl glucoside. Preferred are glyceryl mono- or dioleate, or a mixture thereof with a $C_{8-20}$ alkyl glucoside, in particular coco-glucoside.

As used herein the term '$C_{12-30}$ carboxylic acid' refers to straight (linear) or branch chained alkanoic acids having about 12 up to about 30 carbon atoms. These acids may be saturated or unsaturated, having one or more double bonds and may also contain one or more, e.g. two, hydroxy groups. The term $C_{8-20}$ alkyl or $C_{8-20}$ alkyl refers to straight or branch chained hydrocarbon radicals, saturated or unsaturated, having from about 8 to about 20 or from about 8 to about 16 carbon atoms, including mixtures thereof.

The amount of $C_{12-30}$ carboxylic acid mono- or diglyceride is in the range from 0.01 to 2%, in particular from 0.015 to 1%, preferably from 0.0175 to 0.5%, more preferably in the range from 0.0175 to 0.335%, or from 0.02 to 0.5% still more preferably from 0.08 to 0.2%. The glucoside may be present in the same amounts. All percentages in this paragraph are w/w percentages.

The ratio of the amount of glyceryl mono- or dioleate to the fatty alcohol glucoside for use in the compositions in the products of the invention is in the range from 2:1 to 1:2, preferably in the range from 1.5:1 to 1:1.5, most preferably said ratio is about 1:1. A particularly suited combination is that which is a mixture of 20 to 40% of $C_{12-30}$ carboxylic acid glyceride, 20 to 40% of $C_{8-20}$ alkyl glucoside and water. This particular mixture is added to the compositions in an amount in the range from 0.1 to 1%, preferably from 0.1 to 0.5%, more preferably from 0.25 to 0.5%.

A particularly preferred combination is that which is sold under the trademark 'Lamesoft™', in particular 'Lamesoft PO65™', a mixture of 20 to 40% of glyceryl monooleate, 20 to 40% of coco glucoside and water. This 'Lamesoft' product is added to the compositions in an amount in the range from 0.1 to 1%, preferably from 0.1 to 0.5%, more preferably from 0.25 to 0.5%.

Active Ingredients

Products having a composition that contains one or more active ingredients constitute particularly attractive embodiments of the present invention.

The active ingredients, which may be lipophilic or hydrophilic, can be mixed with or incorporated into suitable carriers. These comprise any skin-acceptable inert materials that are known for formulating active ingredients. The carriers can be finely or more coarsely divided powders, or even granulates. They can comprise starches, sugars, binders, lubricants, diluents, fillers, disintegrating agents, granulating agents and the like components. The nature of the carrier materials will depend on the active ingredient that is formulated therein and on the type of formulation that is desired. Particular carriers for incorporating active ingredients are beads wherein the active ingredient is entrapped in some form.

Examples of active agents which may be hydrophobic or hydrophilic for use in the products of the invention comprise anti-microbials, e.g. anti-bacterials and antifungals, anti-inflammatory agents, anti-irritating compounds, anti-itching agents, moisturising agents, skin caring ingredients, plant extracts, vitamins, and the like. Examples of such ingredients comprise complexes of PVP and hydrogen peroxide, anti-inflammatories as, plant extracts, bisabolol, panthenol, tocopherol, actives for anti-stinging, anti-irritants, anti-dandruffs, for anti-ageing e.g. retinol, melibiose etc. Other suitable actives are e.g. *Medicago officinalis, Actinidia chinensis*, allantoin, *Aloe barbadensis, Anona cherimolia, Anthemis nobilis, Arachis hypogaea, Arnica montana, Avena sativa*, beta-carotene, bisabolol, *Borago officinalis*, butylene glycol, *Calendula officinalis, Camellia sinensis*, camphor, *Candida bombicola*, capryloyl glycine, *Carica papaya, Centaurea cyanus*, cetylpyridinium chloride, *Chamomilla recutita, Chenopodium quinoa, Chinchona succirubra, Chondrus crispus, Citrus aurantium dulcis, Citrus grandis, Citrus limonum, Cocos nucifera, Coffea arabica, Crataegus monogina, Cucumis melo*, dichlorophenyl imidazoldioxolan, *Enteromorpha compressa, Equisetum arvense*, ethoxydiglycol, ethyl panthenol, farnesol, ferllic acid, *Fragaria chiloensis, Gentiana lutea, Ginkgo biloba*, glycerin, glyceryl laurate, *Glycyrrhiza glabra, Hamamelis virginiana*, heliotropine, hydrogenated palm glycerides, citrates, hydrolyzed castor oil, hydrolyzed wheat protein, *Hypericum perforatum, Iris florentina, Juniperus communis*, lactis proteinum, lactose, *Lawsonia inermis*, linalool, *Linum usitatissimum*, lysine, *Magnesium aspartate, magnifera indica, Malva sylvestris*, mannitol, mel, *Melaleuca alternifolia, Mentha piperita*, menthol, menthyl lactate, *Mimosa tenuiflora, Nymphaea alba*, olaflur, *Oryza sativa*, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, *Persea gratissima*, petrolatum, potassium aspartate, potassium sorbate, propylene glycol, *Prunus amygdalus* dulcis, prunus armeniaca, *Prunus persica*, retinyl palmitate, *Ricinus communis, Rosa canina, Rosmarinus officinalis*, rubus idaeus, salicylic acid, *Sambucus nigra*, sarcosine, *Serenoa serrulata, Simmondsia chinensis*, sodium carboxymethyl betaglucan, sodium cocoyl amino acids, sodium hyaluronate, sodium palmitoyl proline, stearoxytrimethylsilane, stearyl alcohol, sulfurized TEA-ricinoleate, talcum, thymus vulgaris, *Tilia cordata*, tocopherol, tocopheryl acetate, trideceth-9, *Triticum vulgare*, tyrosine, undecylenoyl glycine, urea, *Vaccinium myrtillus*, valine, zinc oxide, zinc sulfate and the like.

Of particular interest are active ingredients that can be used for treating skin that shows inflammatory reactions, that is irritated, red or damaged. Examples of such agents are zinc compounds or sulphur.

The active ingredients can be present, depending on the nature of the ingredients and their application, in various concentrations, but usually are present in a quantity in the range of 0.01-10% (w/w), preferably from 0.1-7% (w/w) and more preferably 1-5% (w/w), w/w expressed to the total weight of the lipid or to the compositions.

Typical examples of anti-microbial agents are those active against gram-positive bacteria such as 2,4,4'-trichloro-2'-hydroxydiphenyl ether, chlorohexidine (1,6-di-(4-chlorophenylbiguanido)hexan) or TCC (3,4,4'-trichlorocarbanilide). Furthermore many odorants and etheric oils have anti-microbial activity. Typical xamples are the active ingredients eugenol, menthol and thymol in clove, mint and thyme oil. Further interesting natural deodorizing agents having anti-microbial properties are the terpene alcohol farnesol (3,7,11-trimethyl-2,6,10-dodecatrien-1-ol) and chitosan. Also glycerine monolaurate, glycerine stearate, glycerine oleate as well as glycerine dioleate have been found to possess anti-microbial activity and are particularly attractive for use in products that are applied on babies because of their mildness and lack of side effects. The quantity of anti-microbial agents can vary but usually is in the range of about 0.1 to 2% (w/w)—relative to the total amount of the lipid and/or the compositions The lipid and/or compositions can further contain one or more moisturizers. These are added to improve the sensoric properties as well as to regulate skin hydration. These agents additionally can improve the penetration of the composition in or into the sheet. Moisturizers typically are present in quantities of 1-20% (w/w), preferably of 5-15% (w/w), and more preferably 5-10% (w/w) relative to the total amount of the compositions.

Suitable moisturizers are a.o. ammo acids, pyrrolidone carbonic acid, lactic acid and its salts, lactitol, urea and urea derivatives, ureic acid, glucosamine, creatinine, hydrolysis products of collagen, chitosan or chitosan salts/-derivatives, and in particular polyols and polyol derivatives (e.g. ethylene glycol, propylene glycol, butylene glycol, pentylene glycol, hexylene glycol, erythrite, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20, PEG-135, PEG 150), sugar and sugar derivatives (a.o. fructose, glucose, maltose, maltitol, mannite, inosite, sorbite, sorbityl silandiol, sucrose, trehalose, xylose, xylit, glucuronic acid and its salts), ethoxylated sorbitol (Sorbeth-6, Sorbeth-20, Sorbeth-30, Sorbeth-40), honey and hydrogenated honey, hydrogenated starch hydrolysates, as well as mixtures of hydrogenated wheat protein, hydrolyzed milk protein, lecithin, pythantriol, hyaluronic acid and salts thereof, and PEG-20-acetate copolymers. Particularly preferred moisturizers are glycerine, diglycerine and triglycerine.

The products according to this invention can be used as antiperspirants or deodorants, in particular as wipes or tissues for use in these applications. In products for these applications the compositions contain actives that have deodorizing and/or antiperspirant properties such as, for example, aluminium chlorohydrates, aluminium-zirconium-chlorohydrate as well as zinc salts.

The products according to the invention can also be used in sunscreen applications and in that instance take the form of sunscreen wipes. In these products the lipid and/or compositions contain sunscreen filters which can be organic substances. Either UVA or UVB-filters or both, or inorganic pigments such as titaniumdioxide.

As self-tanning agents there can be added dihydroxy acetone.

The lipid and/or compositions may contain cosmetically acceptable dyes which can be present in quantities in the range of 0.001 to 0.1% (w/w), relative to the total quantity of the lipid and/or compositions.

Application of the Compositions

The compositions may be applied to the sheet using methods generally known in the art for applying aqueous or non-aqueous compositions. For liquid compositions or semi-solid compositions that are not too viscous techniques such as spraying, dripping, immersing and the like can be applied. A preferred application method for the compositions is by spraying with a suitable nozzle or by dripping, for example by using a perforated tube having holes or slits. The immersing technique can be done by running the sheets through a bath holding the compositions and subsequently controlling the amount of liquid that is absorbed by pressing. The amount of such liquid or semi-solid compositions on the wipe may be in the range from about 100 to about 400%, preferably from about 200% to about 400%, expressed as the weight of the composition relative to the weight of the sheet in dry condition.

The compositions may be applied in various ways, evenly or non-evenly, continuously or non-continuously, at the surface or surface portion or, preferably, throughout the whole of the sheet material. Optionally some parts of the sheet can be left dry, i.e. not having the composition. Compositions may be applied at both sides or only at one side of the sheet.

The compositions that are solid or semi-solid can be applied in various amounts, for example in an amount from about 0.1 g to about 10 g per gram of substrate and is typically applied in an amount from about 1.0 g to about 10 g per gram of substrate, preferably from about 2.0 g to about 5 g per gram of substrate, most preferably from about 2 g to about 4.5 g per gram of dry substrate, most preferably about 3.7 to about 3.8 g per gram substrate. Or, the compositions is applied in an amount of about 4 to about 8 g per wipe sized 17.2×21 cm, most preferably about 6 g per wipe.

The compositions that are semi-solid or solid may be applied to the sheet in various ways. Such compositions can be applied by any method that allows coating of the composition material onto the surface of the sheet. As used herein the term 'coating' refers to printing, covering, overlaying, finishing, spraying, extruding, laminating or any other method of applying the phase to the surface of the sheet. Still another technique is based on traditional printing technologies which comprise, for example, screen printing, roller printing and gravure printing.

They also can be applied at the surface or at the surface portion of the sheet, on one or on both sides. They can be applied evenly or non-evenly to the sheet, non-evenly meaning that the distribution of the amount of the composition varies over the area of the sheet, i.e. some areas of the sheet can have greater or lesser amounts of the composition. Preferably the composition is evenly applied to the area of the sheet.

The compositions can be applied discontinuously or continuously to one or both sides of the sheet, or it may even be applied as a complete covering of one or both surfaces of the fabric.

The compositions may be applied to defined parts or regions of the sheet which may take a variety of forms. Particular forms in which the composition may be applied are, e.g. stripes, dots or spots, geometric configurations, either of regular or irregular shape, for example circles, ellipses, squares, rectangles and the like, logos, text, letters or any other non-continuous pattern. The composition may be present as discrete stripes which can be disposed discontinuously, i.e. interrupted, or preferably continuous over the whole surface of the wipe. The stripes may also form a pattern of discrete segments which collectively comprise a stripe or they may have a repetitive pattern such as a sinusoidal shape or wave-like and the like pattern. If waving stripes are selected, preferably the stripes are in phase, so that parallelism is maintained and each stripe remains equally spaced from the adjacent stripes. The stripes are preferably oriented in the machine direction, for ease of manufacture.

The compositions that are semi-solid or solid are typically applied in an amount of about 3 to 40 g/m², preferably from about 10 to about 20 g/m², either on one side or, preferably, on both sides of the sheet. Or, alternatively, such compositions are applied in an amount of about 0.06 g to 0.8 g per gram of substrate, preferably from about 0.20 g to 0.40 g per gram of dry substrate.

Manufacture

In a further aspect the invention concerns a process for preparing a product comprising a sheet as defined herein and a composition, said process comprising contacting a sheet with a composition as described herein. In particular said process comprises impregnating a sheet with a composition as described herein, or in particular impregnating or spraying a wipe with a liquid composition This invention further concerns a process for preparing a product as defined herein, said process comprising coating a porous or absorbent sheet with a solid or semi-solid composition as described herein.

In a particular execution, the sheet is cut into stripes the transversal size of which being similar to the size of the end product, in particular of the tissue or wipe. Subsequently the carrier stripes are folded according to methods generally known and applied in the art. The thus folded stripes are moistened with a liquid composition as described herein, said moistening preferably comprising spraying or dripping. Or the fabric stripes can first be moistened and subsequently be folded. The stripes can also be impregnated with the composition by immersing in or running the strip through a bath containing the composition. They can also be coated, e.g. by spraying or printing, with the composition.

In a further step, the stripes are cut so that the desired size of the sheets, in particular of the wipes, is obtained. The thus obtained sheets (or wipes) can be packed individually or can be stacked in a determined number, e.g. a number between 10 and 30, preferably between 15 and 25, most preferably about 20, or a number between 50 and 100, preferably between 60 and 80, most preferably about 72, and the stack then packed in a suitable package, for example a plastic wrap, box and the like.

The compositions can be applied to the sheet at any time during the manufacturing process of the sheet. Preferably the compositions are applied to the sheet after finishing the manufacturing process of the sheet, more preferably after the sheet has been dried. The compositions may also be applied to the sheet material just after its manufacture while still being wet.

Use and Properties

The sheets according to the invention can take the form of baby or adult wipes and can be used in a wide range of applications as personal care products. The products of the invention may be used as cleansing tools, however their use is not limited to this application only. They may find use as applicators of active substances, in particular of the active substances mentioned herein, or they find use as combined cleanser and applicator of active substances. The sheets may find use as wipes in a wide variety of applications, comprising, for example, baby cleansing wipes, face or body cleansing wipes, wipes for skin treatment or skin conditioning such as, for example, skin moisturization and against skin aging, insect repellent wipes, powder wipes, toilet wipes, antiperspirant wipes, peeling wipes, after-sun treatment wipes, sunscreen wipes, wipes for feminine hygiene, nappy rash wipes, the latter preferably containing zinc oxide as active ingredient, and the like.

The raised regions in the sheets in accordance with the present invention are of lower density as the lowered regions and absorb more of the compositions, in particular of liquid compositions, loaded in or on the sheet. These compositions therefore are concentrated at the raised regions of the sheet which happen to be the parts of the sheet that are in contact with the skin upon usage of the sheet. Consequently, there will be a more intense contact of the skin with the raised regions of the sheet where the compositions are concentrated and there will be a higher release of the compositions to the skin at the raised regions. If these compositions are cleansing compositions, in particular liquid cleansers, this will result in a more effective cleansing. Where these compositions contain certain ingredients that have caring properties, or in particular where these compositions contain active ingredients, the sheet products having such compositions have a more effective transfer of caring ingredients or of active ingredients to the skin. Therefore the sheets in accordance with the present invention are a more efficient vehicle for cleanser, caring ingredients, or active ingredients or a combination of these. The sheet products of this invention additionally provide a more even distribution of any caring or active ingredients on the skin.

The sheet products of the present invention have superior properties in terms of softness and feel. They offer a softer feel of the fabric due to the modification of the fabric surface caused by the specific embossing. The products moreover offer gentler cleansing because of less friction of the wipe on the skin (softer skin-feel).

The products of this invention are particularly attractive because they allow convenient and quick application, and an easier and more evenly distribution of the product. They moreover are easy to apply on babies and children.

In view of these beneficial properties, the products of this invention can be used in a wide variety of cosmetic and personal care applications, but they may also find use in cleaning applications such as cleaning of hard surfaces.

The softness of sheet products can be demonstrated by a number of tests. One such test comprises mounting the sheet to a longitudinal plate at one end of which an object of defined mass is placed. Subsequently that end of the plate is lifted until the object starts gliding downwardly. The angle of the plate at the moment where the weight starts gliding is measured and compared with that of standard sheets.

EXAMPLES

The following examples are given with the nomenclature of INCI.

Example 1

Staple fibers of polyethylene/polypropylene and rayon are processed in a carding machine to produce a web. The carding machine comprises a hopper feeder with a vibrating chute disposed below same which transfers the fibers spread evenly over the width having a surface weight of 50 g/m² to the carding machine with the carding and spiked rollers. A continuous belt subsequently transfers the laid carded non-woven to a calendering device and subsequently to an hydro-entanglement device where partial hydro-entanglement takes place. Then the thus pre-consolidated web is transferred to a second calendering device and subsequently to a combined hydro-entanglement/embossing device. The latter comprises a drum equipped at its surface with a bronze mesh with a wavy pattern. This drum is surrounded by three sets of water jets, each set comprising a series of water jets positioned transversally across the drum at a distance of about 1 cm. The jets in the next series of water jets is positioned about ⅓ of a cm from the previous ones so that after passing all three series the whole surface of the web is compressed and hydro-entangled. In this step, hydro-entanglement is completed at the same time as embossing takes place. After this step, the consolidated web is dried.

Example 2

Dry hydro-entangled sheet material made as described in example is cut into stripes. A liquid composition, having the composition as set forth below in example 3, is sprayed in the conventional manner. Liquid addition was set at 6 g per wipe. Subsequently the stripes are folded and cut.

Example 3

| Composition A | |
|---|---|
| Aqua | 96.336% |
| Polysorbate 20 | 0.600% |
| PEG-75 Lanolin | 0.100% |
| Perfume | 0.150% |
| PEG-40 Hydrogenated Castor Oil | 0.400% |
| Propylene Glycol | 1.120% |
| Phenoxyethanol | 0.800% |
| Tetrasodium EDTA | 0.078% |
| Chamomilla Recutita | 0.070% |
| Ethoxydiglycol | 0.171% |
| Butylene Glycol | 0.035% |
| Glucose | 0.016% |
| Iodopropynyl Butylcarbamate | 0.010% |
| PEG-4 Laurate | 0.090% |
| Citric Acid | 0.020% |
| Composition B | |
| Aqua | 98.252% |
| Phenoxyethanol | 0.800% |
| Iodopropynyl Butylcarbamate | 0.010% |
| PEG-4 Laurate | 0.090% |
| Perfume | 0.150% |
| Tetrasodium EDTA | 0.078% |
| Citric Acid | 0.020% |
| Polysorbate 20 | 0.600% |
| Composition C | |
| Aqua | 97.250% |
| Glycerine | 1.000% |
| Phenoxyethanol | 0.800% |
| Iodopropynyl Butylcarbamate | 0.010% |
| PEG-4 Laurate | 0.090% |
| Perfume | 0.150% |
| Tetrasodium EDTA | 0.078% |
| Citric Acid | 0.020% |
| Polysorbate 20 | 0.600% |
| Composition D | |
| Aqua | 96.332% |
| Glycerine | 1.000% |
| Phenoxyethanol | 0.800% |
| Polysorbate 20 | 0.600% |
| PPG-15 Stearyl Ether | 0.400% |
| PEG-7 Glyceryl Cocoate | 0.100% |
| Propylene Glycol | 0.350% |
| Iodopropynyl Butylcarbamate | 0.010% |
| PEG-4 Laurate | 0.090% |
| Chamomilla Recutita | 0.070% |
| Perfume | 0.150% |
| Tetrasodium EDTA | 0.078% |
| Citric Acid | 0.020% |
| Composition E | |
| Aqua | 97.33% |
| Phenoxyethanol | 0.800% |
| Polysorbate 20 | 0.600% |
| Sorbeth-30 | 0.400% |
| Propylene Glycol | 0.350% |
| Dimethicone Copolyol | 0.100% |
| Iodopropynyl Butylcarbamate | 0.010% |
| PEG-4 Laurate | 0.090% |
| Chamomilla Recutita | 0.070% |
| Perfume | 0.150% |
| Tetrasodium EDTA | 0.078% |
| Citric Acid | 0.020% |

The above-listed formulations are prepared by mixing the components in the sequence of their listing.

The invention claimed is:

1. A non-woven sheet comprising a substrate wherein the non-woven sheet is obtained by carding, spunlaying, meltblowing, wetlaying or a mixture thereof as the web forming procedure and by hydro-entanglement as the web bonding process and wherein a substantial portion of one or both surfaces of the sheet has a three-dimensional pattern embossed therein, said pattern comprising a series of raised and lowered regions, wherein both surfaces have a ridged pattern and none of the raised or lowered regions has any flat portion; wherein the lowered and raised regions are arranged in a recurrent pattern of lowered and raised regions of about the same size and shape and wherein the basis weight of the substrate is essentially the same over the whole surface and wherein the density of the raised regions is in the range of from 20 to 120 kg/m$^3$ and the density of the lowered regions is in the range of from 120 to 180 kg/m$^3$.

2. A non-woven sheet, according to claim 1, obtained by:
providing a precursor substrate, —providing a forming member, having an image surface, and having a three-dimensional pattern engraved therein, said pattern comprising a series of raised and lowered regions, —advancing said precursor substrate onto said three-dimensional transfer device, and applying hydraulic energy to said precursor substrate to simultaneously entangle the fibers of the precursor substrate to furnish the substrate and impart a three-dimensional pattern to the substrate comprising a series of raised and lowered regions, wherein the basis weight of the substrate is essentially the same over the whole surface and wherein the density of the raised regions is lower than the density of the lowered regions.

3. The sheet according to claim 2 wherein the cross-sections of at least a portion of at least one lowered region predominantly exhibit a rounded shape being at least partially flattened at its bottom part.

4. The sheet according to claim 2 wherein the three dimensional pattern is present over the whole surface of the sheet and wherein the embossed pattern may be present at one surface or at both surfaces of the sheet.

5. The sheet according to claim 2 wherein the raised and lowered regions are located adjacent to one another.

6. The sheet according to claim 2 wherein the raised and lowered regions form one or more patterns that are present at one or at both surfaces of said sheet, wherein different patterns are adjacent to one another or are separated by areas that have no pattern.

7. The sheet according to claim 1 wherein the raised and lowered regions form a pattern of lines or stripes.

8. The sheet according to claim 1 wherein the raised and lowered regions run in parallel.

9. The sheet according to claim 1 wherein at least one of the surfaces of the sheet in a transversal section has a sinusoidal shape.

10. The sheet according to claim 1 wherein the width of the lowered and of the raised regions is substantially the same over the whole surface of the sheet.

11. The sheet according to claim 1 wherein the density of the lowered regions is in the range from 120 to 170 kg/m3 and wherein the density of the raised regions is in the range from 60 to 90 kg/m3.

12. The sheet according to claim 1 wherein the non-woven sheet is obtained by subjecting at least one fibrous layer of non-woven fibers to carding by use of at least one carding unit to produce a precursor substrate in a web forming step which is subjected to hydro-entanglement.

13. The sheet according to claim 1 wherein the non-woven sheet is obtained by subjecting at least one first fibrous layer of non-woven fibers to carding by use of at least one carding unit to produce a first precursor substrate layer, placing at least one second fibrous layer onto the first precursor substrate layer by airlaying, subjecting at least one third fibrous layer of non-woven fibers to carding by use of at least one carding unit and placing said third precursor substrate layer adjacent to the second precursor substrate layer, furnishing a precursor substrate which is subjected to hydro-entanglement.

14. The sheet according to claim 1 wherein said sheet is dry or impregnated and/or coated with a suitable composition.

15. The sheet according to claim 14 wherein the composition is an aqueous liquid or an oil-based liquid.

\* \* \* \* \*